(12) United States Patent
Kim et al.

(10) Patent No.: US 7,520,982 B2
(45) Date of Patent: Apr. 21, 2009

(54) CUCURBITURIL-CONTAINING POLYMER, STATIONARY PHASE AND COLUMN USING THE SAME

(75) Inventors: Kimoon Kim, Pohang (KR); Dong Hyun Oh, Pohang (KR); Erumaipatty Rajagounder Nagarajan, Pohang (KR); Young Ho Ko, Pohang (KR); Shashadhar Samal, Pohang (KR)

(73) Assignee: Postech Foundation, Pohang (KR)

( * ) Notice: Subject to any disclaimer, the term of this patent is extended or adjusted under 35 U.S.C. 154(b) by 304 days.

(21) Appl. No.: 10/565,908

(22) PCT Filed: Jul. 24, 2004

(86) PCT No.: PCT/KR2004/001845

§ 371 (c)(1),
(2), (4) Date: Jan. 25, 2006

(87) PCT Pub. No.: WO2005/010058

PCT Pub. Date: Feb. 3, 2005

(65) Prior Publication Data

US 2006/0201862 A1 Sep. 14, 2006

(30) Foreign Application Priority Data

Jul. 26, 2003 (KR) .................. 10-2003-0051840

(51) Int. Cl.
*B01D 15/08* (2006.01)
(52) U.S. Cl. .................... 210/198.2; 210/635; 210/656; 210/502.1
(58) Field of Classification Search .............. 210/502.1, 210/635, 198.2, 656; 502/401
See application file for complete search history.

(56) References Cited

U.S. PATENT DOCUMENTS

| | | | |
|---|---|---|---|
| 4,539,399 A | | 9/1985 | Armstrong |
| 5,276,062 A | * | 1/1994 | Haase .................. 521/25 |
| 5,403,898 A | | 4/1995 | Bradshaw et al. |
| 5,516,766 A | | 5/1996 | Weisz et al. |
| 6,042,723 A | * | 3/2000 | Duval et al. ............ 210/198.2 |
| 6,365,734 B1 | | 4/2002 | Kim et al. |
| 6,398,962 B1 | | 6/2002 | Cabrera et al. |
| 6,869,466 B2 | | 3/2005 | Day et al. |
| 2004/0147396 A1 | | 7/2004 | Richter et al. |
| 2006/0201862 A1 | * | 9/2006 | Kim et al. ............. 210/198.2 |
| 2007/0224403 A1 | * | 9/2007 | Kim et al. ............... 428/220 |

FOREIGN PATENT DOCUMENTS

| | | |
|---|---|---|
| AU | 2002302117 A1 | 3/2003 |
| EP | 1 094 065 A2 | 4/2001 |
| JP | 11-217557 A | 8/1999 |
| KR | 100263872 B1 | 5/2000 |
| WO | WO 00/68232 A1 | 11/2000 |
| WO | 02/096553 A2 | 12/2002 |
| WO | WO 02/096553 A2 | 12/2002 |
| WO | WO 03/055888 A1 | 7/2003 |
| WO | WO 02/096553 | * 12/2005 |

OTHER PUBLICATIONS

Snyder (Introduction to Modern Liquid Chromatography, John Wiley &Sons, Inc. New York, 1979, pp. 177-183).*
Clennan, E.L., et al., "Additions of Singlet Oxygen to Alkoxy-Substituted Butadienes. An Unexpectedly Large s-Cis/s-Trans Ratio in an (E,Z)-Diene or a Kinetic Anomeric Effect?", J. Org. Chem. 1986, 51, pp. 1440-1446.
Kellersberger, K.A., et al. "Encapsulation of $N_2$, $O_2$ Methanol, or Acetonitrile by Decamethylcucurbit[5]uril$(NH_4+)_2$ Complexes in the Gas Phase: Influence of the Guest on 'Lid' Tightness", J. Am. Chem. Soc. 2001, 123, pp. 11316-11317.
Liu et al., Preparation and characterization of perhydroxyl-cucurbit[6]uril bonded silica stationary phase for hydrophilic-interaction chromatography. Talanta 2004, vol. 64, pp. 929-934, XP-002404747.
Nagarajan et al., "Cucurbituril anchored silica gel" Tetrahedron Letters, 2006, vol. 47, pp. 2073-2075.
"Amberlite XAD Polymeric Resins" Product Information, Sigma-Aldrich, Mar. 20, 1998, 3 pages.
Lee et al., "Cucurbituril Homologues and Derivatives: New Opportunities in Supramolecular Chemistry," Acc. Chem. Res., vol. 36, No. 8, 2003, pp. 621-630.

* cited by examiner

*Primary Examiner*—Ernest G Therkorn
(74) *Attorney, Agent, or Firm*—Rothwell, Figg, Ernst & Manbeck, P.C.

(57) ABSTRACT

Provided is a cucurbituril-containing polymer. The cucurbituril-containing polymer may be used in removal, separation, or purification of air pollutants, water contaminants, biological substances, organic or inorganic substances, alkaline metals, heavy metals, ionic or water-soluble biological substances. The cucurbituril-containing polymer may be a stationary phase that may be used for column chromatography.

8 Claims, No Drawings

CUCURBITURIL-CONTAINING POLYMER, STATIONARY PHASE AND COLUMN USING THE SAME

CROSS-REFERENCE TO RELATED APPLICATIONS

This application is a 35 U.S.C. 371 National Phase Entry Application from PCT/KR2004/001845, filed Jul. 24, 2004, designating the U.S.

BACKGROUND OF THE INVENTION

1. Field of the Invention

The present invention relates to a cucurbituril-containing polymer, a stationary phase and a column using the same. The present invention relates to a cucurbituril-containing polymer, a stationary phase and a column using the same. More particularly, the present invention relates to a cucurbituril-bonded polymer, a cucurbituril derivative-containing copolymer, a stationary phase and a column using the polymer or the copolymer, which are useful for separation and removal of substances.

2. Description of the Related Art

Generally, a column packing material is a material that is used as a stationary phase upon separation and purification of various test samples. Various column packing materials in which various compounds are bonded to silica gels have been developed as stationary phases. Crown ether (Korean Patent No. 0263872) and cyclodextrin (U.S. Pat. No. 4,539,399) are known as a representative material bonded to a silica gel. A silica gel bonded with crown ether or cyclodextrin is used as a stationary phase in separation of various test samples by selective non-covalent interactions with various organic or ionic compounds.

Like cyclodextrin, it is known that cucurbituril has retention capacity for various compounds due to the presence of hydrophilic and hydrophobic cavities. However, unlike cyclodextrin, cucurbituril has carbonyl groups on the entrance of the cavities, and thus, can retain various ionic compounds and high polarity compounds by charge-polarity interactions, polarity-polarity interactions, or hydrogen bonds. Therefore, cucurbituril has retention capacity for various compounds, for example, organic compounds such as gaseous compounds, aliphatic compounds, and aromatic compounds, insecticides, herbicides, amino acids, nucleic acids, ionic compounds, metal ions, or organic metal ions (J. Am. Chem. Soc. 2001, 123, 11316; European Patent No. 1094065; J. Org. Chem. 1986, 51, 1440). However, there exist few solvents capable of solubilizing cucurbituril. Furthermore, cucurbituril contains no substituents, and thus, has an extremely limited application, such as a covalent linkage with solids such as silica gel or polymers.

An example of utilization of cyclodextrin-containing polymer as a stationary phase is reported (U.S. Pat. No. 5,403, 898). A stationary phase based on such cyclodextrin-containing polymer can be used in separation of various water-soluble compounds by reverse-phase column chromatography (U.S. Pat. No. 5,516,766). However, as described above, since cyclodextrin has weaker non-covalent binding capacity with various biochemical substances or ions, relative to cucurbituil, its utility is limited.

Recently, there has been an increasing interest in a monolithic column due to its more efficient and rapid separation capacity (U.S. Pat. No. 6,398,962). However, no cucurbituril derivatives have been reported until recently, and thus, there are no studies about preparation of monolithic columns using cucurbituril.

International Patent Application No. PCT/DE02/01980 discloses a silica gel physically coated with cucurbituril prepared by adding the cucurbituril and silica gel to a solvent followed by thermal treatment. However, since the physical coating is not covalent-binding, there are limitations for reproducibility and chemical and physical stability. International Patent Application No. PCT/KR02/02213 discloses a method for preparing hydroxycucurbituril. This method can overcome the above-described disadvantages of cucurbituril. Hitherto, however, there are no reports about separation of various water-soluble substances on a reverse-phase column containing a polymer covalently bonded with cucurbituril derivative.

SUMMARY OF THE INVENTION

The present invention provides a polymer covalently bonded with cucurbituril.

The present invention also provides a copolymer of cucurbituril and organic monomer.

The present invention also provides a silica gel, alumina, and titanium oxide, each of which is coated with a cucurbituril-containing polymer.

The present invention also provides a monolithic column prepared by copolymerization of a cucurbituril derivative and a monomer in a capillary tube or a column tube.

The present invention also provides a column stationary phase for substance separation using one selected from a polymer covalently bonded with cucurbituril, a cucurbituril-containing copolymer, a copolymer of Cucurbituril and organic monomer, and a silica gel, alumina, and titanium oxide, each of which is linked with the polymer or the copolymer.

DETAILED DESCRIPTION OF THE INVENTION

According to an aspect of the present invention, there is provided a polymer in which a cucurbituril derivative of Formula 1 below is covalently bonded to a particle-type polymer with an end-substituted group:

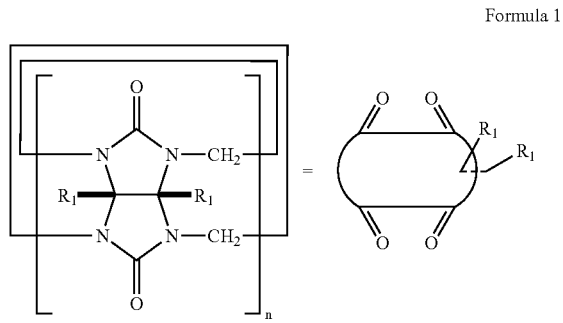

Formula 1 wherein n is an integer of 4 to 20, and each $R_1$ is independently a substituted or unsubstituted alkenyloxy group of $C_2$-$C_{20}$ with an unsaturated bond end, a carboxyalkylsulfanyloxy group with a substituted or unsubstituted alkyl moiety of $C_2$-$C_{20}$, a carboxyalkyloxy group with a substituted or unsubstituted alkyl moiety of $C_2$-$C_8$, an aminoalkyloxy group with a substituted or unsubstituted alkyl moiety of $C_1$-$C_8$, a hydroxyalkyloxy group with a substituted or unsubstituted alkyl moiety of $C_1$-$C_8$, or an epoxyalkyloxy group with a substituted or unsubstituted alkyl moiety of $C_2$-$C_8$.

In the present invention, the particle-type polymer is a polymer used in preparation of the polymer containing the cucurbituril derivative of Formula 1 and can have different end-substituted groups. The particle-type polymer is a polymer that is used as a column packing material, and in particular, has an end functional group such as a halogen atom, a substituted or unsubstituted amino group, an epoxy group, a carboxyl group, thiol, isocyanate, and thioisocyanate. By way of examples, the particle-type polymer is a chlorine-containing Merrifield polymer or an XAD polymer with a chloro group.

To ensure a uniform result when used as a column packing material, the particle-type polymer has preferably an average particle size of 5-300 μm. Such a particle-type polymer is linked with the cucurbituril derivative of Formula 1 by a covalent bond through various organic reactions. The covalent bond may be an ether bond, a sulfanyl bond, an amino bond, an ester bond, an amide bond, a thioamide bond, or a urea bond. Such bond formation will be described hereinafter in more detail.

The cucurbituril-bonded polymer in which the cucurbituril derivative of Formula 1 is covalently bonded to the particle-type polymer with an end functional group may be a compound of Formula 2 below:

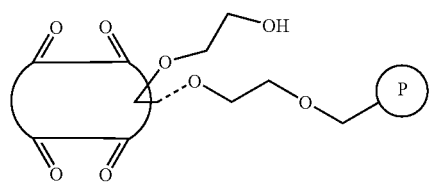

Formula 2 wherein P is a polymer residue obtained from a polymeric particle with a surface halogen group. The compound of Formula 2 may be obtained by ether bond formation between a cucurbituril derivative of Formula 1 and a polymeric particle.

In detail, the compound of Formula 2 may be prepared by stirring a cucurbituril derivative of Formula 1 where $R_1$ is a 2-hydroxyethyloxy group with a polymeric particle, which has been incubated in a reaction solvent for one day, at 60° C. or more in the presence of a base for 20 hours or more, followed by washing with water and acetone. Here, the polymeric particle may be a polymer with a surface halogen atom such as chlorine, iodine, and bromine, for example, a Merrifield polymer. The base may be selected from various bases such as potassium carbonate, potassium chloride, sodium chloride, sodium carbonate, and pyridine. The reaction solvent may be dimethylsulfoxide, dimethylformamide, or water.

The cucurbituril-bonded polymer in which the cucurbituril derivative of Formula 1 is covalently bonded to the particle-type polymer may also be a compound of Formula 3 below:

Formula 3

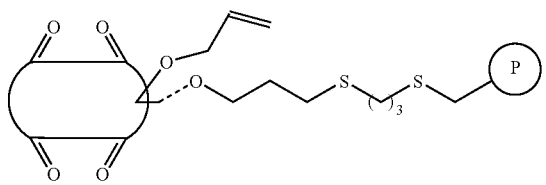

The compound of Formula 3 is obtained by sulfanyl bond formation between a cucurbituril derivative of Formula 1 and a particle-type polymer P with an end-substituted group, in detail, by radical reaction between a polymer P with a thiol group and a cucurbituril derivative of Formula 1 where $R_1$ is an allyloxy group. At this time, the radical reaction is performed by UV irradiation or a radical initiator such as AIBN (2,2'-azobisisobutyronitrile). A solvent that can be used in the radical reaction is an organic solvent such as methanol, chloroform, or acetonitrile.

The cucurbituril-bonded polymer in which the cucurbituril derivative of Formula 1 is covalently bonded to the particle-type polymer may also be a compound of Formula 4 below:

Formula 4

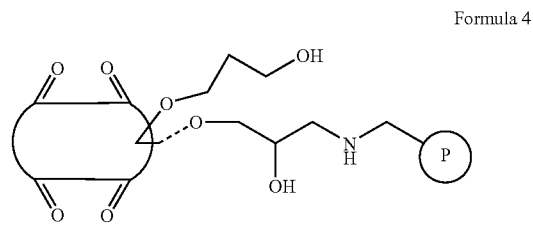

The compound of Formula 4 is obtained by amino bond formation between a cucurbituril derivative of Formula 1 and a polymer, in detail, by reaction between a polymer P ended with a substituted or unsubstituted amino group and a cucurbituril derivative of Formula 1 where $R_1$ is an epoxy group of $C_2$-$C_8$. At this time, the reaction may be carried out in the presence of a base such as triethylamine or pyridine, or alternatively, at high temperature of 50□ or more in the absence of a base.

A solvent that can be used in the amino bond formation is an organic solvent such as dimethylformamide or dimethylsulfoxide. After reaction termination, when the compound of Formula 4 is treated with an aqueous solution of 1M HCl, a remaining epoxy group of the compound of Formula 4 is hydrolyzed, resulting in amino bond formation between another particle-type polymer and the cucurbituril derivative of the compound of Formula 4.

According to another aspect of the present invention, there is provided a polymer of Formula 5 or 6 below, which is obtained by copolymerization between a cucurbituril derivative of Formula 1 and a monomer.

Formula 5

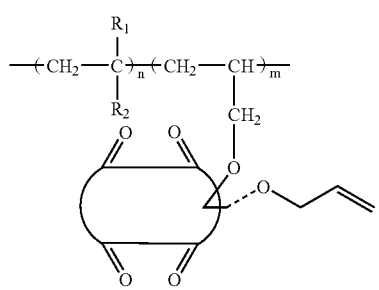

wherein each of n and m is the number of monomer units, n is an integer of 100-10,000, m is an integer of 10-5,000, $R_1$ and $R_2$ are each independently a substituted or unsubstituted aryl group of $C_6$-$C_{30}$, a carboxyl group, a substituted or unsubstituted heterocycle group of $C_4$-$C_{30}$, a substituted or unsubstituted alkyl group of $C_1$-$C_{20}$, a halogen atom, a cyano group, an amino group, a substituted or unsubstituted aminoalkyl group of $C_1$-$C_{10}$, a hydroxyl group, a substituted or unsubstituted hydroxyalkyl group of $C_1$-$C_{10}$, a substituted or unsubstituted alkenyl group of $C_3$-$C_{10}$, or hydrogen.

Preferably, the cucurbituril derivative of Formula 1 used in the compound of Formula 5 has m of 4-20. Preferably, in the compound of Formula 5, when $R_1$ is hydrogen, $R_2$ is phenyl, carboxyl, amide, methylester, or pyrrolidinone, and when $R_1$ is methyl, $R_2$ is carboxyl or amide.

The compound of Formula 5 may be prepared by copolymerization between a cucurbituril derivative of Formula 1 where $R_1$ is an allyloxy group and a monomer $R_1R_2C=CH_2$ ($R_1$ and $R_2$ are as defined above) of Formula 5. Here, the monomer is alkenide with the above-described substituent, for example, styrene, acrylic acid, methacrylic acid, vinylpyrrolidinone, methylacrylate ester, divinylbenzene, or acrylamide. The compound of Formula 5 may be synthesized by stirring 1 mole of allyloxycucurbituril and 5-50 moles of the monomer in an appropriate solvent in the presence of a radical initiator for 10-50 hours.

The solvent may be water or an organic solvent. In the case of using an organic solvent, a mixture of acetonitrile and toluene (100: 0-1,000) may be used. The composition of the organic solvent may be determined considering a particle size according to the purpose of use.

The radical initiator as used in preparation of the compound of Formula 5 may be selected from various radical initiators. Preferably, AIBN, $K_2S_2O_8$, $(NH_4)_2S_2O_8$, or benzoylperoxide may be used. The copolymerization may be carried out at high temperature of 60-80° C. in a nitrogen or argon atmosphere.

For the copolymerization for preparation of the compound of Formula 5, common double-bond copolymerization, for example, radical reaction, Grubb's catalytic reaction, or metallocene reaction, may be used unlimitedly.

Formula 6

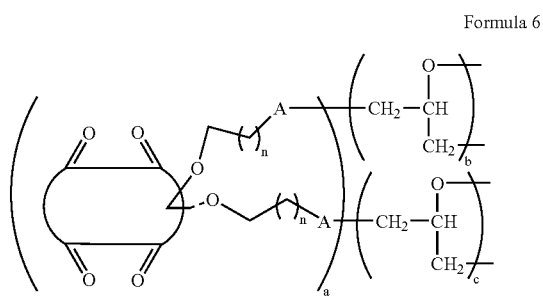

wherein A is NH or O, n is an integer of 1-8, and a is an integer of 10-2,000, b and c represent the number of monomer units and are each independently an integer of 100-10,000.

The polymer of Formula 6 may be synthesized by copolymerization between a cucurbituril derivative of Formula 1 where $R_1$ is an aminoalkyloxy group or a hydroxyalkyloxy group with an alkyl moiety of $C_2$-$C_9$ and epichlorohydrin or epibromohydrin. The copolymerization may be carried out in a solvent such as dimethylformamide, dimethylsulfoxide, ethanol, and water. The base may be pyridine, triethylamine, or potassium carbonate. In the absence of the base, the copolymerization may be carried out at 30-60° C.

It will be understood by one of ordinary persons skilled in the art that in addition to the compounds of Formulae 5 and 6, various cucurbituril-containing polymers can be prepared by known copolymerization between various cucurbituril derivatives and various monomers.

According to another aspect of the present invention, there is provided an alumina, silica gel, or titanium oxide coated with the polymer of Formula 5 or 6.

The polymer of Formula 5 or 6 selected according to the purpose of use is dissolved in a solvent. A silica gel, titanium oxide, or alumina is added to the reaction solution and stirred for 20-40 hours in a sealed state. A polymer solution is removed from the resultant solution by centrifugation or filtration and a remained silica gel, alumina, or titanium oxide is several times washed with the previously used solvent. The solvent may be selected from acetonitrile, acetone, water, and dimethylsulfoxide.

According to another aspect of the present invention, there is provided a compound of Formula 7 in which the polymer of Formula 5 is covalently bonded to a titanium oxide, alumina, or silica gel:

Formula 7

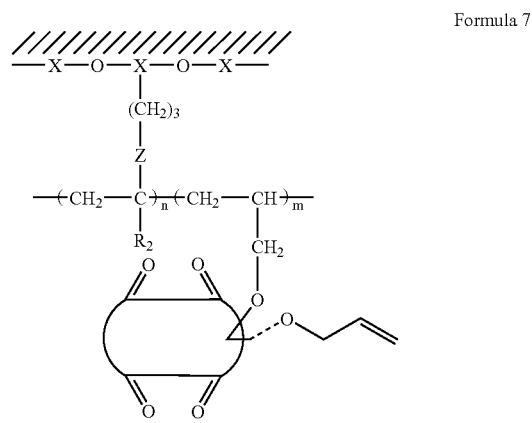

wherein each of n and m is the number of monomer units, n is an integer of 100-10,000, and m is an integer of 10-5,000. A cucurbituril derivative of Formula 1 where n is an integer of 4-20 is used. In the compound of Formula 7, each $R_2$ is independently a substituted or unsubstituted aryl group of $C_6$-$C_{30}$, a carboxyl group, a substituted or unsubstituted heterocycle group of $C_4$-$C_{30}$, a substituted or unsubstituted alkyl group of $C_1$-$C_{20}$, a halogen atom, a cyano group, an amino group, an aminoalkyl group of $C_1$-$C_{10}$, or hydrogen, X is Si, Al, or Ti, and Z is amide, ester, urea, thiourea, amine, or ether.

In preparation of a silica gel of Formula 7 where X is Si, there may be used a silica gel with an end functional group of $C_3$-$C_{10}$ such as amine, isocyanate, isothiocyanate, thiol, hydroxy, or carboxylic acid, and a polymer of Formula 5 where each $R_2$ is a carboxyl group, amine of $C_2$-$C_{10}$, a hydroxyl group, or an alkenyl group. The polymer and the silica gel can be appropriately linked by a common covalent bond.

For example, the silica gel of Formula 7 where X is Si may be prepared by amide bond formation between a silica gel having aminopropyl group and a cucurbituril-containing polymer of Formula 5 where $R_1$ is a carboxyl group.

The amide bond formation may be carried out in a solvent such as methylene chloride, chloroform, dimethylsulfoxide, or water in the presence of dicyclohexylcarbodiimide or 1-[3-(dimethylamino)propyl-3-ethylcarbodiimide for 2-20 hours with stirring. The above-described preparation method of the silica gel of Formula 7 may be applied in preparation of an alumina. That is, an alumina of Formula 7 where X is Al may be prepared by amide bond formation between an alumina having aminopropyl group and a cucurbituril-containing polymer of Formula 5. According to the above-described method, a titanium oxide of Formula 7 where X is Ti may also be prepared. Furthermore, the above-described method may also be applied in preparation of various filter materials such as glass wool, filter paper, or cellulose covalently bonded with a cucurbituril derivative or a cucurbituril-containing polymer.

According to another aspect of the present invention, there are provided a monolithic column including the polymer of Formula 5 or 6 and a preparation method thereof.

According to the present invention, a monolithic column including only a polymer can be prepared as follows: first, a monomer with a substituted or unsubstituted alkenyl group of $C_3$-$C_{20}$ and allyloxycucurbituril of Formula 1 where $R_1$ is an allyloxy group are dissolved in a solvent. Then, a porogen determining the sizes of pores of the polymer and a radical initiator (0.2-5% by weight, based on the total mass of reactants) are sequentially added thereto. The reaction solution is input in a stainless steel column tube with a sealed end, a diameter of 4-12 mm, and a length of 30-100 mm. The other end of the stainless steel column tube is sealed and then the reaction solution is stirred at 60-80° C. for 15-30 hours. After reaction termination, the stainless steel column tube is washed with a solvent such as isopropanol, methanol, or water, at a flow rate of 0.1-10 mL/min. This completes a monolithic column of the present invention. The monomer as used herein is a compound with a substituted or unsubstituted alkenyl group of $C_3$-$C_{20}$ and is preferably one or more selected from acrylamide, acrylic acid, methacrylic acid, methacrylamide, vinylpyrrolidinone, styrene, methylenebisacrylamide, and methacrylbutylester. The solvent may be dimethylsulfoxide or dimethylformamide. The porogen may be a primary alcohol of $C_2$-$C_{18}$, methylene chloride, or chloroform, and the radical initiator may be AIBN, $K_2S_2O_8$, ammonium persulfate, or benzoylperoxide.

A monolithic column according to the present invention can also be prepared as follows: a solution of silane with an alkenyl group of $C_3$-$C_{20}$ in acetone is allowed to flow down through a capillary tube for 10-30 minutes and both ends of the capillary tube are sealed. After incubation of 10-30 hours, the inside of the capillary tube is washed with acetone and water. A radical initiator, a monomer with an alkenyl group, and allyloxycucurbituril of Formula 1 where $R_1$ is an allyloxy group, are dissolved in water or a mixed solvent of water and acetone, and added to the capillary tube. Both the ends of the capillary tube are sealed and polymerization is allowed at room temperature for 10-30 hours. The capillary tube is then washed with a solvent such as water, methanol, or acetonitrile to complete a monolithic column.

According to yet another aspect of the present invention, there is provided a stationary phase for column chromatography using a polymer selected from the polymers of Formulae 2 through 6.

As described above with reference to Formulae 2 through 6, a cucurbituril-containing polymer can be prepared by covalent attachment of a cucurbituril derivative to a polymeric particle with different substituted groups or copolymerization between a cucurbituril derivative and different monomers. The cucurbituril-containing polymer thus prepared can be coated on or covalently bonded to silica gel, alumina, or titanium oxide.

The cucurbituril-containing polymer selected from Formulae 2 through 6, the silical gel, alumina, or titanium oxide linked with the cucurbituril-containing polymer, is packed in a column tube for column chromatography to prepare a column stationary phase. The cucurbituril-containing polymer can be directly used as a stationary phase for column chromatography. The silica gel, alumina, or titanium oxide, which is coated with or covalently bonded with the cucurbituril-containing polymer, can also be used as a stationary phase for column chromatography. The stationary phase thus prepared can be directly used as a column packing material for column chromatography such as HPLC (High Performance Liquid Chromatography), GC (Gas Chromatography), CE (Capillary Electrophoresis), or CEC (Capillary Electrokinetic Chromatography). Therefore, such column chromatography can be efficiently used in separation of alkaline metals and their isotopes; removal and separation of heavy metals; removal of water contaminants and air pollutants; separation and purification of biological substances such as proteins and polypeptides; and the like.

Substituents as used herein are defined as follows. The alkyl group refers to a straight or branched chain radical of $C_1$-$C_{20}$, preferably a straight or branched chain radical of $C_1$-$C_{12}$. More preferably, the alkyl group is a lower alkyl of $C_1$-$C_6$. Examples of the alkyl group include methyl, ethyl, n-propyl, isopropyl, n-butyl, isobutyl, sec-butyl, t-butyl, pentyl, iso-amyl, and hexyl. A lower alkyl radical of $C_1$-$C_3$ is more preferable. One or more hydrogen atoms on the alkyl group, preferably 1-5 hydrogen atoms, may be substituted by a halogen atom, an amino group, an alkylamino group of $C_1$-$C_{10}$, a nitro group, a hydroxyl group, a carboxyl group, a cyano group, an alkoxy group of $C_1$-$C_{10}$, an alkenyl group of $C_2$-$C_{10}$, a heterocycle group of $C_4$-$C_{36}$, an aryl group of $C_6$-$C_{30}$, or a heteroaryl group of $C_4$-$C_{30}$.

The aryl group as used herein, which is used alone or in combination, refers to a carbocyclic aromatic system of 6-30 carbon atoms containing one or more rings. The rings may be attached to each other as a pendant group or may be fused. The term "aryl" comprehends an aromatic radical such as phenyl, naphthyl, tetrahydronaphthyl, indane, and biphenyl. Phenyl is preferable. One or more hydrogen atoms on the aryl group, preferably 1-5 hydrogen atoms, may be substituted by a halogen atom, an amino group, a nitro group, a hydroxyl group, a carboxyl group, a cyano group, an alkylamino group of $C_1$-$C_{10}$, an alkyl group of $C_1$-$C_{10}$, a haloalkyl group of $C_1$-$C_{10}$, an alkoxy group of $C_1$-$C_{10}$, or an alkenyl group of $C_2$-$C_{10}$.

The heterocycle group as used herein refers to a saturated, partially saturated, or unsaturated cyclic radical of $C_4$-$C_{30}$ containing a hetero atom selected from nitrogen, sulfur, silicon, phosphorus, and oxygen. Examples of the saturated heterocycle radical include a saturated 3- to 6-member heteromonocycle group containing 1-4 nitrogen atoms (e.g., pyrrolidinyl, imidazolidinyl, piperidino, piperazinyl); a saturated 3- to 6-member heteromonocyclyl group containing 1-2 oxygen atoms and 1-3 nitrogen atoms (e.g., morpholinyl); and a saturated 3- to 6-member heteromonocyclyl group containing 1-2 sulfur atoms and 1-3 nitrogen atoms (e.g., thiazolidinyl). Examples of the partially saturated heterocycle radical include dihydrothiophene, dihydropyrane, dihydrofurane, and dihydrothiazole. Examples of the unsaturated heterocycle group (also called as heteroaryl group) include an unsaturated 5- and 6-member heteromonocyclyl group containing 1-4 nitrogen atoms, such as pyrrolyl, pyrrolinyl, imidazolyl, pyrazolyl, 2-pyridyl, 3-pyridyl, 4-pyridyl, pyrimidyl, pyrazinyl, pyridazinyl, and triazolyl (e.g., 4H-1,2,4-triazolyl, 1H-1,2,3-triazolyl, 2H-1,2,3-triazolyl); an unsaturated condensed heterocycle group containing 1-5 nitrogen atoms, such as indolyl, isoindolyl, indolyzinyl, benzimidazolyl, quinolyl, isoquinolyl, indazolyl, benzotriazolyl, and tetrazolopyridazinyl (e.g., tetrazolo [1,5-b]pyridazinyl); an unsaturated 3- to 6-member heteromonocyclyl group containing oxygen, such as pyranyl, 2-furyl, and 3-furyl; an unsaturated 5- and 6-member heteromonocyclyl group containing sulfur atom, such as 2-thienyl and 3-thienyl; an unsaturated 5- and 6-member heteromonocyclyl group containing 1-2 oxygen atoms and 1-3 nitrogen atoms, such as oxazolyl, isoxazolyl, and oxadiazolyl (e.g., 1,2,4-oxadiazolyl, 1,3,4-oxadiazolyl, 1,2,5-oxadiazolyl); an unsaturated condensed heterocycle group containing 1-2 oxygen atoms and 1-3 nitrogen atoms (e.g., benzoxazolyl, benzoxadiazolyl); an unsaturated 5- and 6-member heteromonocyclyl group containing 1-2 sulfur atoms and 1-3 nitrogen atoms, such as thiazolyl and thiadiazolyl (e.g., 1,2,4-thiadiazolyl, 1,3,4-thiadiazolyl, 1,2,5-thiadiazolyl); and an unsaturated condensed heterocycle group containing 1-2 sulfur atoms and 1-3 nitrogen atoms (e.g., benzothiazolyl, benzothiadiazolyl). The heterocycle group comprehends a heterocycle radical fused with an aryl radical. Examples of such a fused bicyclic radical include benzofuran and benzothiophene. The heterocycle group may have a mono- to tri-substituted group selected from lower alkyl, halogen atom, hydroxy, oxo, amino, and lower alkylamino. Preferably, the heterocycle radical comprehends 5- to 10-member fused or unfused radicals. More preferably, examples of the heteroaryl group include benzofuryl, 2,3-dihydrobenzofuryl, benzothienyl, indolyl, dihydroindolyl, chromanyl, benzopyrane, thiochromanyl, benzothiopyrane, benzodioxolyl, benzodioxanyl, pyridyl, thienyl, thiazolyl, oxazolyl, furyl, and pyrazinyl. Still more preferably, the heteroaryl radical has one or more hetero atoms selected from sulfur, nitrogen, and oxygen and is a 5- or 6-member heteroaryl selected from thienyl, furanyl, pyrrolyl, thiazolyl, oxazolyl, imidazolyl, pyrazolyl, isoxazolyl, isothiazolyl, pyridyl, piperidinyl, and pyrazinyl.

The alkenyl group as used herein refers to a straight or branched aliphatic hydrocarbon of $C_3$-$C_{20}$ containing a carbon-carbon double bond. Preferably, the alkenyl group has 2-12 carbon atoms, and more preferably, 2-6 carbon atoms. A branched alkenyl group refers to a straight alkenyl group attached with one or more lower alkyl groups or lower alkenyl groups. The alkenyl group may be unsubstituted or substituted by one or more of halo, carboxy, hydroxy, formyl, sulfo, sulfino, carbamoyl, amino, and imino, but are not limited thereto. Examples of the alkenyl group include ethenyl, prophenyl, carboxyethenyl, carboxyprophenyl, sulfinoethenyl, and sulfonoethenyl.

It will be understood by those of ordinary skill in the art that various changes will be made in a method for preparing a cucurbituril-containing polymer, a method for synthesizing a column packing material using the polymer, and a method for preparing a stationary phase for column chromatography, according to the present invention.

Hereinafter, the present invention will be described by Examples to more specifically illustrate a method for synthesizing various polymers and a method for preparing a monolithic column according to the present invention.

EXAMPLES

Example 1

Preparation of Particle-Type Polymer Linked with Cucurbituril by Ether Bond 1 g (1 mmol) of Merrifield polymeric particles (100-200 meshes, 1 mmol/g Cl) were added to 120 mL of dimethylsulfoxide and stirred for 20 hours. 17 g (10 mmol) of 2-hydroxyethyloxycucurbit[6]uril of Formula 1 where n is 6 and $R_1$ is an 2-hydroxyethyloxy group and then 276 mg (2 mmol) of potassium carbonate were added and stirred at 60° C. for 20 hours. After the reaction terminated, the resultant solution was washed with dimethylsulfoxide, water, methanol, acetone, and diethylether (twice for each) to give 105 mmol/g of a particle-type polymer linked with cucurbituril by an ether bond, as represented by Formula 2.

$^{13}$C-CP MAS NMR(300 MHz): δ154.2, 143.2, 139.5, 133.2, 128.4, 120.5, 119.3, 118.7, 98.5, 69.5, 43.2, 42.2, 39.6, 29.5.

Elemental analysis: C 83.03%, N 3.38%, H 7.01%

Example 2

Preparation of Copolymer of Cucurbituril and Styrene 170 mg (0.1 mmol) of allyloxycucurbit[6]uril of Formula 1 where n is 6 and $R_1$ is an allyloxy group and 120 μl of styrene were dissolved in a mixed solvent of 5 mL acetone and 5 mL water. 3 mg of $K_2S_2O_8$ was added to the reaction mixture and stirred at 75° C. for 24 hours in a nitrogen atmosphere. After the reaction terminated, the resultant solution was washed with water, acetone, methanol, and diethyl ether (three times for each) to give 200 mmol/g of a copolymer of cucurbituril and styrene of Formula 5 where $R_1$ is hydrogen and $R_2$ is a phenyl group.

$^{13}$C-CP MAS NMR (300 MHz): δ156.1, 146.2, 143.3, 140.5, 138.5, 131.9, 128.4, 122.5, 119.3, 117.3, 97.4, 71.2, 68.5, 48.2, 42.2, 39.6, 29.5.

Elemental analysis: C 82.03%, N 6.71%, H 8.71%

Example 3

Preparation of Silica Gel Coated with Cucurbituril-Containing Polymer 200 mg of the copolymer of cucurbituril and styrene of Formula 5 where $R_1$ is hydrogen and $R_2$ is a phenyl group, as prepared in Example 2, was dissolved in 5 mL dimethylsulfoxide, and 100 mg of a silica gel was added to the reaction mixture. A reactor containing the reaction mixture was filled with nitrogen, sealed, and stirred for 24 hours. After the reaction terminated, a solvent and a polymer dissolved in the solvent were removed by centrifugation. The silica gel was washed with dimethylsulfoxide, water, methanol, acetone, and ether (twice for each) in a centrifuge to give a silica gel coated with cucurbituril-containing polymer.

Example 4

Preparation of Silica Gel Covalently Bonded with Cucurbituril-Containing Polymer 100 mg (3.15 mmol/g of carboxylic acid, 315 m mol) of a copolymer of cucurbituril and acrylic acid of Formula 5 where $R_1$ is hydrogen and $R_2$ is a carboxyl group was dissolved in 10 mL of dimethylsulfoxide. 100 mg (1.35 mmol/g of amine group, 135 m mol) of a silica gel having aminopropyl group and then 39 mg (200 m mol) of 1-[3-(dimethylamino)propyl-3-ethylcarbodiimide were added to the reaction mixture and stirred at room temperature for 20 hours. After the reaction terminated, the resultant solution was washed with dimethylsulfoxide, water, methanol, acetone, and diethyl ether (three times for each) to give 458 mmol/g of a silica gel covalently bonded with cucurbituril-containing polymer of Formula 7 where X is Si.

$^{13}$C-CP MAS NMR (300 MHz): δ184.5, 156.1, 138.5, 122.5, 119.3, 97.4, 71.2, 42.2, 29.5.

Elemental analysis: C 31.83%, N 16.43%, H 6.71%

Example 5

Preparation of Capillary Monolithic Column Including Cucurbituril-Containing Copolymer An aqueous solution of 0.2 M sodium hydroxide, an aqueous solution of 0.2 M hydrochloric acid, and distilled water were sequentially allowed to flow down through a capillary tube with 100 μm in diameter and 50 cm in length for 30 minutes (for each) for washing. A 30% by volume solution of 3-(trimethoxysilyl) propylmethacrylate in acetone was then allowed to flow down through the capillary tube for 15 minutes. Both ends of the capillary tube were sealed and the capillary tube was left stand at room temperature for 15 hours. The inside of the capillary tube was washed with methanol and water. 0.2 mg (0.001 mmol) of piperazine diacrylamide, 7.1 mg (0.1 mmol) of acrylamide, and 17 mg (0.01 mmol) of allyloxycucurbit[6]uril of Formula 1 where n is 6 and $R_1$ is an allyloxy group, were dissolved in 3 mL of a phosphate buffer (50 mM, pH 7), followed by de-aeration by a nitrogen gas and addition of 10 μl of 10% ammonium persulfate and 10 μl of 10% tetramethylethylenediamine. The reaction solution was filled in the capillary tube, both the ends of the capillary tube were sealed, and the capillary tube was left stand at room temperature for 20 hours. After copolymerization terminated, distilled water was allowed to flow down through the capillary tube for 30 minutes in a pressure of 150 bar for washing to give a capillary monolithic column including a cucurbituril-containing copolymer.

Example 6

Preparation of Column Including Cucurbituril-Containing Polymer 400 mg of a silica gel linked with cucurbituril-containing polymer of Formula 2 in which the silica gel is covalently bonded to the cucurbituril-containing polymer was added to 10 mL of methanol. A column tube with 8 mm in diameter and 4.5 cm in length was treated with high frequency for 10 minutes and an end of the column tube was sealed with a glass wool. The previously prepared reaction solution was allowed to flow down through the column tube to form a column tube packed with a stationary phase selected from the silica gel linked with the cucurbituril-containing polymer. The column tube packed with the stationary phase was several times washed with methanol, acetone, and diethyl ether, and dried to give a column for column chromatography.

Cucurbituril as a host molecule has excellent non-covalent binding capacity with various guest molecules in an aqueous solution. In this regard, a polymer containing such cucurbituril can be used as a stationary phase for reverse-phase column chromatography or in a monolithic column in which its application range is increasing rapidly. The thus-prepared stationary phase can be more efficiently used in removal or separation of various water-soluble substances such as contaminants, ionic substances, biological substances, organic and inorganic substances, and metal ions, relative to a currently available cucurbituril-bonded silica gel.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A polymer in which a particle-type polymer with a reactive end-substituted group is linked to a cucurbituril derivative of Formula 1 below by a covalent bond:

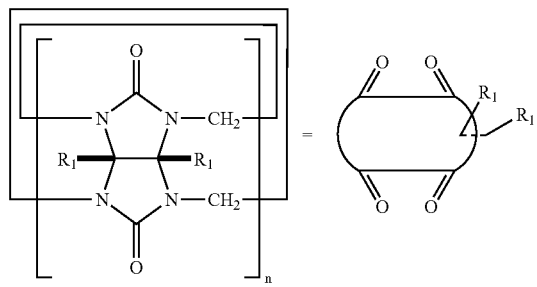

(1)

wherein n is an integer of 4 to 20, and each $R_1$ is independently a substituted or unsubstituted alkenyloxy group of $C_2$-$C_{20}$ with an unsaturated bond end, a carboxyalkylsulfanyloxy group with a substituted or unsubstituted alkyl moiety of $C_2$-$C_{20}$, a carboxyalkyloxy group with a substituted or unsubstituted alkyl moiety of $C_2$-$C_8$, an aminoalkyloxy group with a substituted or unsubstituted alkyl moiety of $C_1$-$C_8$, a hydroxyalkyloxy group with a substituted or unsubstituted alkyl moiety of $C_1$-$C_8$, or an epoxyalkyloxy group with a substituted or unsubstituted alkyl moiety of $C_2$-$C_8$.

2. The polymer of claim 1, wherein the reactive end-substituted group is a halogen atom, a substituted or unsubstituted amino group, an epoxy group, a carboxyl group, a thiol group, an isocyanate group, or a thioisocyanate group.

3. The polymer of claim 1, wherein the particle-type polymer with the reactive end-substituted group is a selected from the group consisting of a Merrifield polymer, a hydrophobic polyaromatic polymer, and an acrylic ester polymer.

4. The polymer of claim 1, wherein the particle-type polymer has an average particle size of 5-300 μm.

5. The polymer of claim 1, wherein the covalent bond is an ether bond, a sulfanyl bond, an amino bond, an ester bond, an amide bond, a thioamide bond, or a urea bond.

6. A polymer in which the cucurbituril derivative of Formula 1 of claim 1 is copolymerized with a monomer with a substituted or unsubstituted alkenyl group of $C_3$-$C_{20}$.

7. The polymer of claim 6, which is a compound of Formula 5 below:

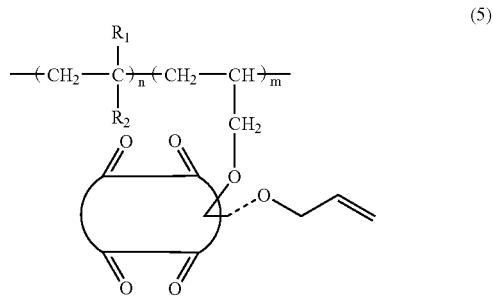

(5)

wherein n is an integer of 100-10,000, m is an integer of 10-5,000, $R_1'$ and $R_2'$ are each independently a substituted or unsubstituted aryl group of $C_6$-$C_{30}$, a carboxyl group, a substituted or unsubstituted heterocycle group of $C_4$-$C_{30}$, a substituted or unsubstituted alkyl group of $C_1$-$C_{20}$, a halogen atom, a cyano group, an amino group, a substituted or unsubstituted aminoalkyl group of $C_1$-$C_{10}$, a hydroxyl group, a substituted or unsubstituted hydroxyalkyl group of $C_1$-$C_{10}$, a substituted or unsubstituted alkenyl group of $C_3$-$C_{10}$, or hydrogen.

8. The polymer of claim 7, wherein the cucurbituril derivative of Formula 1 of claim 1 where $R_1$ is an allyloxy group is copolymerized with the monomer with a substituted or unsubstituted alkenyl group of $C_3$-$C_{20}$.

* * * * *